United States Patent [19]
Knauf-Beiter et al.

[11] Patent Number: 6,130,236
[45] Date of Patent: *Oct. 10, 2000

[54] PESTICIDAL COMPOSITIONS

[75] Inventors: Gertrude Knauf-Beiter, Müllheim, Germany; Jürg Speich, Basel, Switzerland

[73] Assignee: Novartis Finance Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/171,341

[22] PCT Filed: Apr. 21, 1997

[86] PCT No.: PCT/EP97/02009

§ 371 Date: Oct. 13, 1998

§ 102(e) Date: Oct. 13, 1998

[87] PCT Pub. No.: WO97/40683

PCT Pub. Date: Nov. 6, 1997

[30] Foreign Application Priority Data

Apr. 30, 1996 [CH] Switzerland .............................. 1093/96

[51] Int. Cl.$^7$ ............................. A01N 43/64; A01N 43/78
[52] U.S. Cl. ............................................ 514/366; 514/383
[58] Field of Search ...................... 514/366, 383

[56] References Cited

FOREIGN PATENT DOCUMENTS

2 199 748   7/1988   United Kingdom .

OTHER PUBLICATIONS

Tomlin, The Pesticide Manual Incorporating the Agrochemicals Handbook, 10$^{th}$ Ed. (1995) pp. 1017 & 1018.
Chemical Patents Index, Documentation Abstracts Journal, No. 94–299637, Nov. 16, 1994.
Database World Patent Index Abstr. No. 77–91045y. (1977).
Woloshuk, et al., "The Effect of Three Fungicides, Specific for the Control of Rice Blast Disease, on the Growth and Melanin Biosynthesis by Pyricularia oryzae Cav.," Pesticide Science, vol. 12, No. 1, pp. 86–90 (1981).

*Primary Examiner*—Allen J. Robinson
*Attorney, Agent, or Firm*—Michael P. Morris

[57] ABSTRACT

The present invention relates to novel crop-protecting active ingredient mixtures having synergistically enhanced action, comprising at least two active ingredient components together with a suitable carrier, wherein component I is 1-[[2-(2,4-dichorophenyl)-4-propyl-1,3-dioxolan-2-yl] methyl]-1H-1,2,4-triazole ("propiconazole")
and component II is
5-methyl-1,2,4-triazolo[3,4-b][1,3]benzothiazole ("tricyclazole");
or in each case a salt or metal complex thereof.

8 Claims, No Drawings

PESTICIDAL COMPOSITIONS

This application is a 371 of PCT/E897/02009, filed Apr. 21, 1997.

The present invention relates to novel crop-protecting active ingredient mixtures having synergistically enhanced action, comprising at least two active ingredient components together with a suitable carrier, wherein component I is 1-[[2-(2,4-dichlorophenyl)-4-propyl-1,3-dioxolan-2-yl] methyl]-1H-1,2,4-triazole ("propiconazole") (ref: Ch. R. Worthing (ed.) The Pesticide Manual, 9th edition, 1991, page 724)

and component II is 5-methyl-1,2,4-triazolo[3,4-b][1,3]benzothiazole ("tricylazole"); (ref: Ch. R. Worthing (ed.):

The Pesticide Manual, 9th edition, 1991, page 846), or in each case a salt or metal complex thereof.

Surprisingly, it has now been found that the mixtures of components I and II according to the invention have, in the prevention and control of plant diseases, not only an additive action but a distinct synergistically enhanced action.

Advantageous mixing ratios of the two active ingredients are I:II=from 30:1 to 1:30, from 1 0:1 to 1:10, preferably I:II=from 3:1 to 1:3 and from 1:1 to 1:3.

The present invention relates also to a method of protecting plants from plant diseases, especially fungal infestation, which comprises treating the plants, parts of plants or their surroundings with a component I and a component II, in any desired sequence or simultaneously.

The active ingredient mixtures I+II according to the invention have very advantageous properties for protecting plants against disease infestation. The active ingredient mixtures in question can be used to inhibit or destroy the micro-organisms that occur on plants or on parts of plants (the fruit, blossom, leaves, stems, tubers or roots) of different crops of useful plants, while at the same time parts of plants that grow later are also protected against such microorganisms. They can also be used as dressings in the treatment of plant propagation material, especially seed (fruit, tubers, grains) and plant cuttings (e.g. rice), to provide protection against fungus infections as well as against phytopathogenic fungi that occur in the soil. The active ingredient mixtures according to the invention are distinguished by the fact that they are well tolerated by plants and are environmentally friendly.

The active ingredient mixtures are effective against phytopathogenic fungi belonging to the following classes: Ascomycetes (e.g. Venturia, Podosphaera, Erysiphe, Monilinia, Mycosphaerella, Uncinula); Basidiomycetes (e.g. the genus Hemileia, Rhizoctonia, Puccinia); Fungi imperfecti (e.g. Botrytis, Helminthosporium, Rhynchosporium, Fusarium, Septoria, Cercospora, Alternaria, Pyricularia and *Pseudocercosporella herpotrichoides*); and Oomycetes (e.g. Phytophthora, Peronospora, Bremia, Pythium, Plasmopara).

Target crops for the areas of indication disclosed herein comprise within the scope of this invention e.g. the following species of plants: cereals (wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The active ingredient mixtures according to the invention are especially advantageous for the treatment of rice against Pyricularia and Rhizoctonia and also Helminthosporium.

The mixtures of compounds of formulae I and II are normally used in the form of compositions. The compounds of formulae I and II can be applied to the area or plant to be treated either simultaneously or in succession on the same day, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers.

A preferred method of applying an active ingredient mixture comprising at least one of each of the active ingredients I and II is application to the parts of the plants that are above the soil, especially to the leaves (foliar application). The frequency and rate of application depend upon the biological and climatic living conditions of the pathogen. The active ingredients can, however, also penetrate the plant through the roots via the soil or via the water (systemic action) if the locus of the plant is impregnated with a liquid formulation (e.g. in rice culture) or if the substances are introduced in solid form into the soil, e.g. in the form of granules (soil application). In order to treat seed, the compounds of formulae I and II can also be applied to the seeds (coating), either by impregnating the tubers or grains with a liquid formulation of each of the active ingredients in succession, or by coating them with an already combined wet or dry formulation. In addition, in special cases, other methods of application to plants are possible, for example treatment directed at the buds or the fruit trusses.

The compounds of the combination are used in unmodified form or, preferably, together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are generally from 50 g to 2 kg a.i./ha, especially from 100 g to 1000 g a.i./ha, more especially from 250 g to 700 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g. phosphatidylethanolamine, phosphatidylserine, phosphatidylglycerol and lysolecithin.

The agrochemical compositions normally comprise 0.1 to 99%, especially 0.1 to 95%, compounds of formulae I and II, 99.9 to 1%, especially 99.9 to 5%, of a solid or liquid adjuvant and 0 to 25%, especially 0.1 to 25%, of a surfactant.

Whereas commercial products will preferably be formulated as concentrates, the end user will normally employ dilute formulations.

The Examples which follow serve to illustrate the invention, "active ingredient" denoting a mixture of compound I and compound II in a specific mixing ratio.

Formulation Examples

| Wettable powders | a) | b) | c) |
|---|---|---|---|
| active ingredient [I:II = 1:3 (a), 1:2 (b), 1:1 (c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:II = 1:6) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient [I:II = 1:6 (a), 1:2 (b), 1:10 (c)] | 5% | 6% | 4% |
| talcum | 95% | — | — |
| kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| active ingredient (I:II = 2:1) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (I:II = 1:10) | 8% |
| polyethylene glycol (mol. wt. 200) | 3% |
| kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:II = 1:8) | 40% |
| propylene glycol | 10% |
| nonylphenol polyethytene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

A synergistic effect exists whenever the action of an active ingredient combination is greater than the sum of the actions of the individual components.

The action to be expected E for a given active ingredient combination obeys the so-called COLBY formula and can be calculated as follows (COLBY, S.R. "Calculating synergistic and antagonistic responses of herbicide combination". Weeds, Vol. 15, pages 20–22; 1967): ppm=milligrams of active ingredient (=a.i.) per litre of spray mixture X=% action by active ingredient I using p ppm of active ingredient Y=% action by active ingredient II using q ppm of active ingredient.

According to Colby, the expected (additive) action of active ingredients I+II using p+q ppm of active ingredient is $$E = X + Y - \frac{X \cdot Y}{100}$$

If the action actually observed (O) is greater than the expected action (E), then the action of the combination is superadditive, i.e. there is a synergistic effect.

EXAMPLE B-1

Action Against *Puccinia recondita* on Wheat
a) Residual-protective Action
6 days after sowing, wheat plants are sprayed to drip point with an aqueous spray mixture prepared from a wettable powder formulation of the active ingredient mixture and infected 24 hours later with a uredospore suspension of the fungus. After an incubation period of 48 hours (conditions: 95–100% relative humidity at 20°) the plants are placed in a greenhouse at 22°. Fungus infestation is evaluated 12 days after infection.
b) Systemic Action
5 days after sowing, wheat plants are watered with an aqueous spray mixture prepared from a wettable powder formulation of the active ingredient mixture. Care is taken that the spray mixture does not come into contact with parts of the plant that are above the soil. The plants are infected 48 hours later with a uredospore suspension of the fungus. After an incubation period of 48 hours (conditions 95–100% relative humidity at 20°) the plants are placed in a greenhouse at 22°. Fungus infestation is evaluated 12 days after infection. The active ingredient mixtures according to the invention exhibit a good synergistic action.

EXAMPLE B-2

Action Against *Rhizoctonia solani* on Rice Plants

Approximately two-week-old rice plants are placed together with the soil around the roots in a vessel filled with a spray mixture of the active ingredient mixture. After 96 hours, the rice plants are infected with a conidia suspension of the fungus. Fungus infestation is evaluated after incubating the infected plants for 5 days at 95–100% relative humidity and about 24° C. The active ingredient mixtures according to the invention exhibit a distinctly enhanced action.

EXAMPLE B-3

Residual-protective Action Against *Venturia inaequalis* on Apples

Apple cuttings with 10–20 cm long fresh shoots are sprayed to drip point with an aqueous spray mixture prepared from a wettable powder formulation of the active ingredient mixture and infected 24 hours later with a conidia suspension of the fungus. The plants are incubated for 5 days at 90–100% relative humidity and stood in a greenhouse for a further 10 days at 20–24°. Fungus infestation is evaluated 12 days after infection. The active ingredient mixtures according to the invention exhibit a distinctly enhanced action.

EXAMPLE B-4

Action Against *Pyricularia oryzae* on Rice Plants

Approximately two-week-old rice plants are placed together with the soil around the roots in a vessel filled with a spray mixture of the active ingredient mixture. After 96 hours, the rice plants are infected with a conidia suspension of the fungus. Fungus infestation is evaluated after incubating the infected plants for 5 days at 95–100% relative humidity and about 24° C. The results are shown in the following Table.

| propiconazole (mg a.i./l) | tricyclazole (mg a.i./l) | ratio in mixture | % activity observed | % activity expected | SF (Colby) O/E |
|---|---|---|---|---|---|
| 0.6 | | | 0 | | |
| 2 | | | 2 | | |
| 6 | | | 15 | | |
| 20 | | | 22 | | |
| 60 | | | 25 | | |
| | 0.2 | | 3 | | |
| | 0.6 | | 13 | | |
| | 2 | | 59 | | |
| | 6 | | 82 | | |
| 0.6 | 0.2 | 3:1 | 56 | 3 | 18.7 |
| | 0.6 | 1:1 | 60 | 13 | 4.6 |
| | 2 | 1:3 | 72 | 59 | 1.2 |
| | 6 | 1:10 | 88 | 82 | 1.1 |
| 2 | 0.2 | 10:1 | 36 | 5 | 7.2 |
| | 0.6 | 3:1 | 47 | 15 | 3.1 |
| 6 | 0.2 | 30:1 | 36 | 18 | 2.0 |
| | 0.6 | 10:1 | 51 | 26 | 2.0 |
| 20 | 0.6 | 30:1 | 56 | 32 | 1.8 |

What is claimed is:

1. A composition comprising a synergistically effective microbicidal amount of a mixture comprising at least two active ingredient components together with a suitable carrier, wherein component I is 1-[[2-(2,4-dichlorophenyl)-4-propyl-1,3-dioxolan-2-yl] methyl]-1H-1,2,4-triazole and component II is 5-methyl-1,2,4-triazolo[3,4-b][1,3]benzothiazole or in each case a salt or metal complex thereof; wherein the ratio by weight of I:II is from 30:1 to 1:10.

2. A composition according to claim 1, wherein the ratio by weight of I:II is from 10:1 to 1:10.

3. A composition according to claim 2, wherein the ratio by weight of I:II is from 3:1 to 1:3.

4. The composition according to claim 1 further comorising an adjuvant.

5. The composition according to claim 4 wherein the adjuvant comprises a phospholipid.

6. A method of protecting plants from plant diseases, which comprises treating the plants, parts of plants, seeds plant cuttings or their surroundings with a synergistically effective microbicidal amount of a mixture of component I and component II according to claim 1, in any desired sequence or simultaneously.

7. The method according to claim 6 of treating rice to protect the rice against phytopathic fungi selected from the group consisting of Pyricularia, Rhizoctonia, Helminthosporium, and mixtures therof.

8. The method according to claim 6 wherein the treatment comprises a foliar application or a soil application of the mixture of component I and component II.

* * * * *